United States Patent [19]

Lewis et al.

[11] Patent Number: 4,582,835
[45] Date of Patent: Apr. 15, 1986

[54] ANALGESIC COMPOSITIONS

[75] Inventors: John W. Lewis, North Ferriby; John G. Lloyd-Jones, Cottingham, both of England

[73] Assignee: Reckitt & Colman Products Limited, London, England

[21] Appl. No.: 678,478

[22] Filed: Dec. 5, 1984

[30] Foreign Application Priority Data

Dec. 6, 1983 [GB] United Kingdom ............... 8332556

[51] Int. Cl.$^4$ ............................................. A61V 31/44
[52] U.S. Cl. ..................................... 514/282; 424/10; 514/812
[58] Field of Search ................. 424/10, 260; 514/282, 514/812

[56] References Cited

PUBLICATIONS

Chem. Abst. 94-150268y (1984).
Chemical Abstracts 90, 145726j.
Manara et al., Dev. Neurosci, (Amsterdam) 1978, 4 (Charact. Funct. Opioids) 225-6.
Dettmar et al., Biochem. Soc. Trans. 1978, 6(5), 1004-6 (=Chem. Abs. 90, 197597n (1979).
Ramabadran et al., Endog. Exog. Opiate Agonists Antagonists, Proc. Int. Narc. Res. Club. Conf. 1979 (Pub 1980) 471-4 (-Chem. Abs. 94, 15027u (1981)).
Rance et al., Endog. Exog. Opiate Angonists Antagonists, Proc. Int. Narc. Res. Club. Conf. 1979 (Pub 1980) 387-90 (-Chem. Abs., 94, 150268y (1981)).

Primary Examiner—Stanley J. Friedman
Attorney, Agent, or Firm—Bacon & Thomas

[57] ABSTRACT

A method of treating pain which comprises the administration to a patient of a parenterally or sublingually effective dose of buprenorphine together with an amount of naloxone sufficient to prevent substitution in an opiate dependent subject. Preferably when the administration is parenteral the weights of naloxone and buprenorphine are within the ratio of 1:3 to 1:1 and when administered sublingually the weights are within the ratio of 1:2 to 2:1.

4 Claims, 2 Drawing Figures

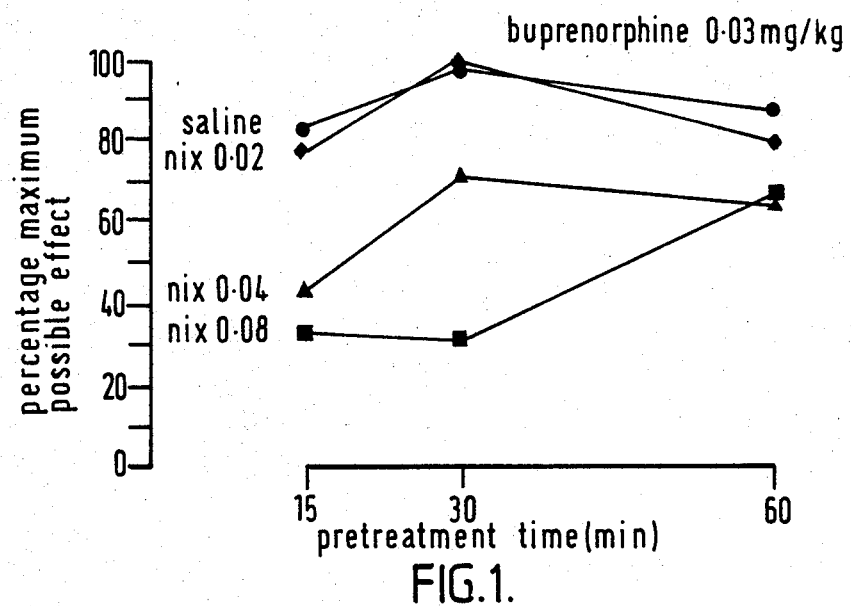
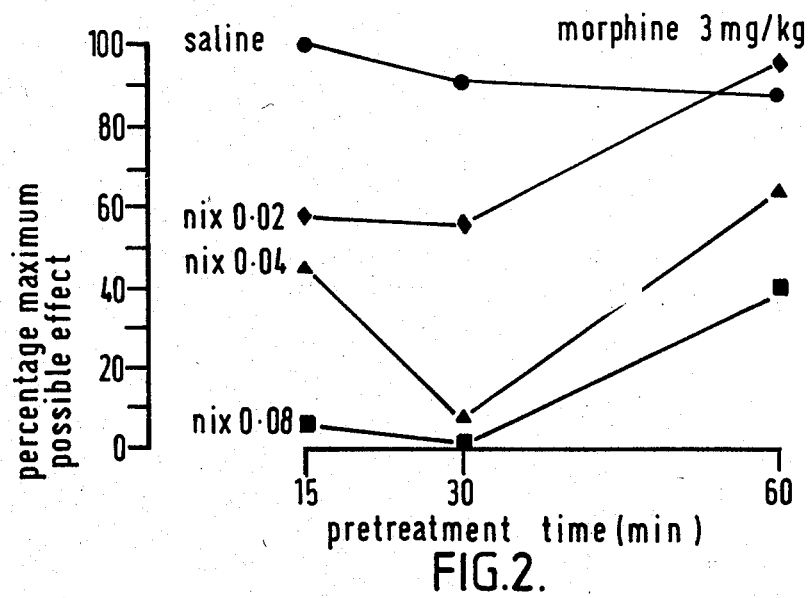

ANALGESIC COMPOSITIONS

This invention relates to analgesic compositions and more particularly to compositions containing buprenorphine.

Buprenorphine (International Non-proprietary Name for N-cyclopropylmethyl-7α-[1-(S)-hydroxy-1,2,2-trimethylpropyl]6,14-endoethano-6,7,8,14-tetrahydronororipavine) has been shown in clinical trials to be a potent antagonist analgesic lacking the psychotomimetic effects found with other antagonist analgesics. Buprenorphine effectively relieves moderate to severe pain in doses of 0.1 mg or more administered either parenterally or sublingually. The optimum therapeutic range for single doses is 0.3 mg–0.6 mg by injection and 0.1 mg–0.4 mg for sublingual tablets.

In animal tests and in man buprenorphine has been shown to have both agonist (morphine-like) and antagonist properties. However from direct dependence studies in animals and in man it has been concluded that buprenorphine does not produce significant physical dependence and the potential to produce psychological dependence is low as indicated by animal self administration studies and by the measurement of euphorigenic effects in human post addicts.

In man the agonist and narcotic antagonist characteristics of buprenorphine have been demonstrated in opiate addicts. In a study in Hong Kong oral buprenorphine in the dose range 6–16 mg precipitated abstinence in opiate addicts presenting for detoxification. On the other hand in a study involving subjects stabilised on a relatively low daily dose of oral methadone, sublingual buprenorphine could be substituted for methadone with only a low level of discomfort. In this situation buprenorphine was behaving as an opiate agonist of low intrinsic activity.

This limited ability of buprenorphine to substitute for the opiates and its low-level opiate-like euphorigenic effects makes buprenorphine acceptable to some opiate misusers particularly when their favoured opiates are unavailable, and this has led to some illicit use of the drug. As will be discussed below the compositions of the present invention provide a means of enhancing the abstinence-precipitating properties of buprenorphine, and thus the aversive characteristics, without compromising its analgesic effect.

Preparations have been developed which protect the oral preparations of certain opioids from parenteral abuse by the incorporation of naloxone. These preparations are based on the low oral bio-availability ($\sim 1\%$) of the narcotic antagonist naloxone (naloxone, chemically known as 1-N-allyl-14-hydroxynordihydro-morphinone) when compared to that of methadone ($\sim 50\%$) and pentazocine ($\sim 30\%$). Thus a significant quantity of naloxone can be introduced into oral preparations of these central analgesics without compromising their analgesic effect. If the opioid-naloxone preparations are dissolved in water and injected the naloxone is active and shows its narcotic antagonist activity. It thus blocks the euphorigenic activity of the opioid and eliminates the development of psychological dependence. The inhibition of opiate effects by naloxone also prevents the development of physical dependence. U.S. Pat. No. 3,773,955 to Pachter and Gordon describes the oral combination of naloxone with a number of opiates particularly methadone.

There are also examples in which naloxone has been incorporated into oral preparations of opioids to prevent primary oral abuse. The combination of tilidine and naloxone affords such an example. Tilidine acting through a metabolite is more potent when given by the oral route than the parenteral route. Consequently no advantage can be gained by the addict in self administration of tilidine by injection and as such the observed abuse of tilidine has been by oral administration. A product containing naloxone was introduced to protect tilidine against this abuse.

U.S. Pat. No. 4,457,933 (issued July 3, 1984) to Pachter and Gordon describes the protection with naloxone of oral dosage forms of various opioids against both oral and parenteral abuse. In this patent mention is made of the incorporation of 1–3 mg of naloxone in an oral unit dose of buprenorphine (2 mg).

To our knowledge there is no reference in the scientific or patent literature to the incorporation of naloxone (for purposes of abuse prevention) into formulations of opioids for parenteral or sublingual administration.

It will be appreciated from the foregoing discussion that when naloxone is combined with an opioid for parenteral administration, the effects of the opioid including its analgesic effect would be expected to be reduced. The literature on the pharmacology of buprenorphine would lead one to conclude that this would be true of buprenorphine. The interaction between buprenorphine and a specific opiate antagonist, diprenorphine when co-administered parenterally has been reported (Cowan et al., Br. J. Pharmacol., 60, 537 (1977)) to result in a reduction in the analgesic potency of buprenorphine by a factor of 300. It would therefore not have been expected that any combination of buprenorphine with naloxone for parenteral administration could be found which would contain sufficient naloxone to be effective in limiting misuse, and would leave the analgesic effect of buprenorphine intact.

Surprisingly, in animal experiments we have now found that there is a limited range of ratios of buprenorphine with naloxone for which, by injection, the analgesic performance is equal to that of buprenorphine alone whilst the abstinence-precipitating effects in opiate-dependent subjects are equivalent to that of naloxone alone. When the opiates such as morphine, methadone, and oxycodone are mixed with naloxone the agonist-antagonist interaction reduces the analgesic performance of the agonist and in complementary fashion reduces the antagonist performance of the naloxone.

There is no teaching in the prior art regarding the protection of preparations of opioids intended for sublingual administration by the incorporation of naloxone. We have found that the bioavailability of naloxone by the sublingual route is very much better (20%) than by the oral route (1%) and thus the concept which was developed by others for the protection of oral opioid preparations against parenteral abuse would not be expected to apply to sublinqual and buccal preparations.

However, the sublingual bioavailability of buprenorphine (50%) is superior to that of naloxone and since we have shown that in a limited range of dosage ratios by parenteral administration naloxone, with full bioavailability, could be combined with buprenorphine without affecting its analgesic performance, we were able to extend our findings to an equivalent limited range of dosage ratios for sublingual and buccal administration which would achieve similar results and afford protection against parenteral misuse.

According to this invention there is provided a method of treating pain which comprises the administration to a patient of a parenterally or sublingually effective dose of buprenorphine together with an amount of naloxone sufficient to prevent substitution in an opiate dependent subject.

This invention also provides an analgesic composition in parenteral or sublingual dosage form comprising an active dose of buprenorphine and an amount of naloxone sufficient to prove aversive to a narcotic addict by parenteral administration but insufficient to compromise the analgesic action of the buprenorphine.

It is to be understood that the use of the terms buprenorphine and naloxone comprehend not only the bases but also their pharmaceutically acceptable salts. Particular preferred salts are the hydrochlorides.

It will be appreciated that the required ratio of naloxone to buprenorphine is dependent upon the proposed route of administration. Preferably the parenteral dosage form contains naloxone and buprenorphine within the weight ratio of 1:3 to 1:1 and the sublingual form within the ratio 1:2 to 2:1.

The ratios were determined in our laboratories according to the following methods.

In the rat tail pressure test (Green, Young, Br. J. Pharmac. Chemother., 6, 572 (1957)) the maximum antinociceptive effect ($ED_{90}$) with buprenorphine was achieved at a dose of 0.03 mg/kg, by subcutaneously administration (s.c.). The equivalent antinociceptive dose of morphine was 3.0 mg/kg. These doses were selected for evaluation of the influence of co-administration of naloxone on the antinociceptive effect of both buprenorphine and morphine. Inclusion of naloxone at the dose of 0.02 mg/kg with the buprenorphine dose produced no significant antagonism (FIG. 1). Increasing the naloxone content to 0.04 and 0.08 mg/kg produced significant antagonism (Dunnett's test) of the antinociceptive effect of buprenorphine at 15 minutes and at these ratios the trend was maintained over 60 minutes.

Naloxone at all three dose levels produced significant falls in the antinociceptive effect of morphine (FIG. 2). These results show that buprenorphine is significantly less sensitive than morphine to the antagonist effects of naloxone. In particular a dose of 0.02 mg/kg of naloxone has no effect on the $ED_{90}$ dose of buprenorphine but it reduces by greater than 30% the antinociceptive action of the equivalent dose of morphine.

The ability to precipitate abstinence in morphine-dependent rats has been evaluated using the method of Teiger D. G., J. Pharmac. exp. Ther. 190, 408 (1974).

Table 1 presents the mean behavioural scores precipitated by intraveneous administration of the challenge drug after 48 hour infusions of 100 mg/kg/24 h of morphine.

TABLE 1

| Challenge Drug | Dose mg/kg | Mean behavioural score | P |
|---|---|---|---|
| Saline | 0.03 | 6.7 | — |
| Buprenorphine | 0.03 | 11.7 | NS |
| Buprenorphine | 0.3 | 14.2 | NS |
| Naloxone | 0.02 | 40.8 | <0.01 |
| Naloxone | 0.2 | 63.3 | <0.01 |
| Buprenorphine + Naloxone | 0.03 0.02 | 31.7 | <0.05 |
| Buprenorphine + Naloxone | 0.3 0.2 | 54.2 | <0.01 |

TABLE 1-continued

| Challenge Drug | Dose mg/kg | Mean behavioural score | P |
|---|---|---|---|
| Naloxone | 0.2 | | |

Buprenorphine (0.03 mg/kg or 0.3 mg/kg) produced only very mild signs of withdrawal, as indicated by low mean behaviour scores. Naloxone (0.02 mg/kg and 0.2 mg/kg) produced rapid and intense abstinence effects which were maintained when combined with buprenorphine in a 2:3 ratio.

This ratio of naloxone to buprenorphine has been evaluated in analgesic studies in patients. The efficacy and safety of buprenorphine (0.3 mg per patient) in combination with naloxone (0.2 mg) was compared with buprenorphine (0.3 mg) alone following intramuscular or intravenous administration to 162 patients with moderate to severe post operative pain. Patients were assessed for pain intensity, pain relief and vital signs (pulse rate and systolic and diastolic blood pressure) at regular intervals for a six hour period after administration. The duration of analgesia was measured by recording the time to analgesic remedication and all unwanted effects occurring during the assessment period were recorded. Both treatments provided good analgesia which lasted for approximately 10–12 hours. Statistical analysis of the efficacy data showed no significant difference between the two treatments for pain intensity, pain relief or duration of analgesia. Analysis of the unwanted effects and vital signs data also showed no significant differences between the two treatments. These results show that the buprenorphine/naloxone combination provides safe and effective analgesia and there is no significant differences between the combination and buprenorphine along with regard to efficacy.

It is preferable to formulate the compositions in unitary dosage forms i.e. physically discrete units containing the appropriate amounts of buprenorphine and naloxone together with pharmaceutically acceptable diluents and/or carriers. Such unitary dosage forms for parenteral administration are suitably in the form of ampoules and for sublingual administration in the form of tablets.

Compositions intended for parenteral administration comprise an isotonic solution of buprenorphine and naloxone in sterile water. Conveniently the solution is made isotonic by use of dextrose and sterilised by autoclaving or by filtration through a membrane filter.

Compositions in the form of sublingual tablets contain soluble excipients such as lactose, mannitol, dextrose, sucrose or mixtures thereof. They will also contain granulating and disintegrating agents such as starch, binding agents such as povidone or hydroxypropyl-methyl cellulose and lubricating agents such as magnesium stearate.

The compositions in unitary dosage form for parenteral administration comprises from about 0.3 to about 0.6 mg buprenorphine together with an amount of naloxone such that the ratio by weight of naloxone to buprenorphine is within the range of 1:3 to 1:1, plus a pharmaceutically acceptable carrier.

The compositions in the form of a sublingual tablet comprise from about 0.1 to about 0.4 mg buprenorphine together with an amount of naloxone such that the ratio by weight of naloxone to buprenorphine is within the range of 1:2 to 2:1, plus at least one pharmaceutically acceptable carrier or diluent.

The invention is illustrated by the following Examples:

EXAMPLE 1

A parenteral formulation having the following composition

|  | mg/ml |
|---|---|
| Buprenorphine HCl | 0.324 |
| Naloxone HCl | 0.3 |
| Anhydrous dextrose | 50.0 |
| Hydrochloric acid to pH | 4.0 |
| Water for injection to | 1.0 ml | was prepared by dissolving dextrose, buprenorphine hydrochloride and naloxone hydrochloride in that order with stirring, in about 95% batch volume of Water for Injection. The acidity of the solution was adjusted to pH 4.0 by the addition of 0.1 M hydrochloric acid, and the solution was made up to volume with Water for Injection. The solution was filtered through a 0.22 μm membrane filter and transferred to sterilised 1 ml or 2 ml glass ampoules containing 1 ml or 2 ml of the solution containing 0.3 or 0.6 mg of buprenorphine base respectively. The ampoules were sealed and the product sterilised by autoclaving.

EXAMPLE 2

The formulation of Example 1 was varied by using 0.15 mg/ml of naloxone hydrochloride instead of 0.3 mg/ml.

EXAMPLE 3

The formulation of Example 1 was varied by using 0.20 mg/ml of naloxone hydrochloride instead of 0.3 mg/ml.

EXAMPLE 4

A sublingual tablet formulation having the following composition

|  | mg/tablet |
|---|---|
| Buprenorphine HCl | 0.216 |
| Naloxone HCl | 0.2 |
| Lactose | 30.934 |
| Mannitol | 18.0 |
| Maize starch | 9.0 |
| Povidone | 1.2 |
| Magnesium stearate | 0.45 |
|  | 60.0 | was prepared by screening all the materials with the exception of the magnesium stearate through a 750 μm seive and blending them together. The mixed powders were then subjected to an aqueous granulation procedure and dried at 50° C. The resulting granules were forced through a 750 μm sieve and blended with magnesium stearate (pre-sieved through a 500 μm sieve). The tablet granules were compressed to yield tablets of 5.56 mm diameter and weight 60 mg.

EXAMPLE 5

The formulation of Example 4 was varied by using 0.4 mg/tablet of naloxone hydrochloride and 30.734 mg/tablet lactose.

EXAMPLE 6

The formulation of Example 4 was varied by using 0.1 mg/tablet of naloxone hydrochloride and 31.034 mg/tablet lactose.

EXAMPLE 7

The formulation of Example 4 was varied by using 0.108 mg/tablet of buprenorphine hydrochloride, 0.1 mg/tablet naloxone hydrochlorite and 31.142 mg/tablet lactose.

We claim:

1. A method of treating pain which comprises the administration to a patient of a parenterally effective unit dosage of buprenorphine wherein the weight of buprenorphine is between about 0.3 to about 0.6 mg and simultaneously an amount of naloxone sufficient to prevent substitution in an opiate dependent subject, the weights of naloxone and buprenorphine administered parenterally being within the ratio of 1:3 to 1:1.

2. A method of treating pain which comprises the administration to a patient of a sublingually effective unit dosage of buprenorphine wherein the weight of buprenorphine is between about 0.1 to about 0.6 mg and simultaneously an amount of naloxone sufficient to prevent substitution in an opiate dependent subject, the weights of naloxone and buprenorphine administered sublingually being within the ratio of 1:2 to 2:1.

3. An analgesic composition in parenteral unit dosage form comprising an active dose of buprenorphine of from about 0.3 to about 0.6 mg and an amount of naloxone sufficient to prove aversive to a narcotic addict by parenteral administration but insufficient to compromise the analgesic action of the buprenorphine, the weights of naloxone and buprenorphine being within the ratio of 1:3 to 1:1.

4. An analgesic composition in sublingual unit dosage form comprising an active dose of buprenorphine of from about 0.1 to about 0.6 mg and an amount of naloxone sufficient to prove aversive to a narcotic addict by parenteral administration but insufficient to compromise the analgesic action of the buprenorphine, the weights of naloxone and buprenorphine being within the ratio of 1:2 to 2:1.

* * * * *